US010476431B1

(12) United States Patent
Alzubi et al.

(10) Patent No.: US 10,476,431 B1
(45) Date of Patent: Nov. 12, 2019

(54) DEVICE AND METHOD FOR MEASURING EFFECT OF SOILING ON PHOTOVOLTAIC DEVICE

(71) Applicant: KUWAIT INSTITUTE FOR SCIENTIFIC RESEARCH, Safat (KW)

(72) Inventors: Feras Ghazi Alzubi, Safat (KW); Abdullah Ramadhan Alkandary, Qortuba (KW); Abdulwahab Tareq Alasfour, Abdulla Al-Mubarak (KW)

(73) Assignee: Kuwait Institute for Scientific Research, Safat (KW)

( * ) Notice: Subject to any disclaimer, the term of this patent is extended or adjusted under 35 U.S.C. 154(b) by 0 days.

(21) Appl. No.: 16/529,717

(22) Filed: Aug. 1, 2019

Related U.S. Application Data (63) Continuation-in-part of application No. 16/244,041, filed on Jan. 9, 2019.

(51) Int. Cl.
*H02S 50/10* (2014.01)
*G01N 21/94* (2006.01)
(Continued)

(52) U.S. Cl.
CPC ............ *H02S 50/10* (2014.12); *G01N 21/94* (2013.01); *G01R 29/24* (2013.01); *H01L 31/02021* (2013.01); *H02S 40/10* (2014.12)

(58) Field of Classification Search
CPC .......... H02S 50/10; H02S 50/00; H02S 10/00; H02S 99/00; H02S 40/10; G01N 21/94;
(Continued)

(56) References Cited

U.S. PATENT DOCUMENTS 4,712,063 A 12/1987 Osterwald et al.
7,062,830 B2 * 6/2006 Alles ..................... F24F 3/0442
236/51
(Continued)

FOREIGN PATENT DOCUMENTS

CN 107774647 A 3/2018
CN 108745998 A 11/2018

OTHER PUBLICATIONS

Micheli et al., "An Investigation of the Key Parameters for Predicting PV Soiling Losses," Progress in Photovoltaics, vol. 25, Issue 4, Jan. 25, 2017, pp. 269-337.
(Continued)

*Primary Examiner* — Jermele M Hollington
*Assistant Examiner* — Taqi R Nasir
(74) *Attorney, Agent, or Firm* — Richard C. Litman; Nath, Golberg & Meyer (57) ABSTRACT

The device and method for measuring the effect of soiling on a photovoltaic device includes a device in which a photovoltaic device (reference solar cell, solar cells, PV module, etc.) may be shifted between partially and fully enclosed compartments in quick succession for measurements of the same device (1) when directly exposed to illumination or solar radiation; (2) when placed under a glass or transparent cover maintained cleared or cleaned of soil; and (3) when placed under glass or transparent cover left exposed to natural outdoor soiling, or attenuated using simulated soil that is not periodically cleaned. The measurements may be of short circuit current ($I_{sc}$), maximum power ($P_{max}$), or other electrical parameter conventionally used to evaluate performance of the photovoltaic device. A soiling ratio calculated as:

(Continued)

$$SR_{Pmax} = 1 - \frac{P_{max2} - P_{max3}}{P_{max1}}$$

or calculated as:

$$SR_{Isc} = 1 - \frac{I_{sc2} - I_{sc3}}{I_{sc1}}$$

may be used to compare or monitor performance of the photovoltaic device between measurement cycles.

15 Claims, 7 Drawing Sheets

(51) Int. Cl.
*H02S 40/10* (2014.01)
*H01L 31/02* (2006.01)
*G01R 29/24* (2006.01)

(58) Field of Classification Search
CPC ... H01L 31/02021; G01R 29/24; G01R 15/08; G01R 15/12; G01R 15/125; G01R 15/165; G01R 15/20; F24F 11/52; F24F 11/32; F24F 11/62; H04L 27/02; H04L 27/04; H04L 27/38; H01R 33/02; H01R 4/48; H01R 11/18
USPC ...... 324/51, 96, 126, 127, 133, 156, 761.01, 324/762.02–762.09; 702/182; 375/240, 375/229, 233, 287, 288; 429/958, 822
See application file for complete search history.

(56) References Cited

U.S. PATENT DOCUMENTS

| | | | |
|---|---|---|---|
| 9,590,559 B2 | 3/2017 | Jarnason et al. | |
| 9,620,663 B2* | 4/2017 | Dror | H01L 31/18 |
| 9,778,306 B1* | 10/2017 | Prod'homme | H02S 50/10 |
| 10,171,029 B2 | 1/2019 | Gostein et al. | |
| 2006/0290343 A1* | 12/2006 | Crafts | G01R 1/073 |
| | | | 324/754.18 |
| 2007/0164771 A1* | 7/2007 | Lin | G01R 31/2846 |
| | | | 324/762.02 |
| 2012/0037181 A1 | 2/2012 | Jia et al. | |
| 2012/0310427 A1* | 12/2012 | Williams | G05F 1/67 |
| | | | 700/287 |
| 2013/0159064 A1 | 6/2013 | Fisher et al. | |
| 2015/0090311 A1 | 4/2015 | Mau et al. | |
| 2015/0280644 A1* | 10/2015 | Gostein | H02S 50/00 |
| | | | 356/72 |
| 2016/0190984 A1* | 6/2016 | Caine | H02S 50/00 |
| | | | 702/60 |
| 2016/0359453 A1* | 12/2016 | Jones | H02S 50/00 |
| 2017/0104451 A1 | 4/2017 | Gostein | |
| 2017/0230001 A1 | 8/2017 | Gostein et al. | |
| 2017/0338771 A1 | 11/2017 | Gostein et al. | |
| 2018/0159469 A1 | 6/2018 | Trupke et al. | |
| 2018/0278202 A1 | 9/2018 | Gostein et al. | |
| 2018/0337633 A1 | 11/2018 | Tamizhmani et al. | |

OTHER PUBLICATIONS

Boeing. "The Impact of Waters of Low Quality on Soiling Removal from Photovoltaic Panels." (2018).

* cited by examiner

DEVICE AND METHOD FOR MEASURING EFFECT OF SOILING ON PHOTOVOLTAIC DEVICE

CROSS-REFERENCE TO RELATED APPLICATION

This application is a continuation-in-part of U.S. patent application Ser. No. 16/244,041, filed on Jan. 9, 2019.

BACKGROUND

1. Field

The present disclosure relates to measuring and testing of photovoltaic devices, and particularly to a device and method for measuring the effect of soiling on a photovoltaic device, such as a reference cell, a solar cell, or a photovoltaic module, to determine the change in electrical characteristics resulting from accumulated dust and other environmental contamination, and further to the evaluation of the effectiveness of anti-soiling solutions and photovoltaics covers.

2. Description of the Related Art

One form of energy generation is the conversion of sunlight to electricity using a photovoltaic (PV) module that consists of electrically connected solar cells. When a group of modules are further connected, a PV system is formed, which typically ranges in size from residential to utility.

When PV systems are installed in outdoor locations, one of the most detrimental environmental factors that affects their performance is the accumulation of soil, which is the settlement of dust particles, debris, and/or other contaminants on the surface of PV modules, otherwise known as soiling. Performance degradation occurs because when particles settle on the surface of PV modules, they interfere with incoming light by blocking, attenuating, and/or scattering it. The power output that is lost as a result is known as the Soiling Loss (SL). Many research groups in dust-intensive regions have reported SL values well above 20%. For example, a PV system that was installed in a desert region tilted at 20°, lost up to 60% of its power after six months of no cleaning.

Such high soiling loss values result in significant revenue deficiencies and excessive operation and maintenance costs. Consequently, there has been a growing interest in quantifying and monitoring such an environmental factor, as the deployment of PV systems in dust-intensive climates is rapidly increasing. This is especially true for utility scale PV systems, as it improves energy prediction models, optimizes PV Plant cleaning strategies, and creates a new performance assessment tool.

Fundamentally, existing soiling detectors are implemented by measuring one of three primary parameters, viz., soil mass; light transmission; or PV performance. The latter parameter has been widely adopted by PV practitioners and researchers for directly measuring the power loss due to soiling. This method of soiling detection measurement involves comparing the power output of an installed reference PV device (i.e., cleaned daily) to a test PV device (i.e., left to naturally soil).

Although performance-based measurements using two PV devices offer a direct way to measure SL, the method involves high uncertainty, since it assumes that the two devices are identical. However, it is well established that PV devices fabricated using the same materials and processes have intrinsic differences. Such differences include (a) Quantum efficiency (QE); (b) Angular response (Ar); (c) Thermal response (Tr); (d) Parasitic resistances (Pr); and how these four parameters change over time.

Therefore, simply comparing two PV devices to measure soiling while neglecting the aforementioned differences will introduce high measurement uncertainty. Using this method, errors as high as 4.5% have been reported. Although a few researchers have considered accommodating such factors, their approaches require intensive periodic in-lab PV assessment, which renders them impractical for long-term monitoring. Furthermore, such an assessment is less than optimum for accommodating the particular environment of a given installation site.

Thus, a device and method for measuring the effect of soiling on a photovoltaic device solving the aforementioned problems are desired.

SUMMARY

The device and method for measuring the effect of soiling on a photovoltaic (PV) device are used to provide data representative of deterioration in performance from soiling of PV devices. A test jig with a test enclosure having first, second and third measurement stations can be used. In this embodiment, the first station is substantially external to the test enclosure and is used to obtain reference values for a PV device as a device under test (DUT); this station will be interchangeably referred to as the initial state hereinafter. The second and third stations are within a test enclosure. A support for the DUT has the capability of transporting the PV device between the first, second and third stations for sequential testing on the same device under different conditions. At the first station, the DUT has substantially full, direct, unobstructed exposure to a light source, defining a first state. At the second station, the DUT has exposure through a transparent cover of the enclosure that is maintained in clean condition, defining a second state. In this regard, the transparent cover of the second compartment is adapted for a wide range of cleaning frequency (minutely, hourly, daily, etc.) At the third station, the DUT has exposure through a transparent cover of the enclosure that has been exposed to natural outdoor soiling, or attenuated using simulated soil, defining a third state. In the first state, the exposure comprises light passed directly to the PV device, substantially without passing through the enclosure. In the second state, the exposure comprises light passed to the PV device through the transparent cover in a clean state. In the third state, the exposure comprises light passed to the photovoltaic device through a transparent cover in a soiled state. A measuring and test unit is configured to measure short circuit current (Isc), maximum power (Pmax), and/or other criteria in the three states in quick succession and report the result in a novel ratio to show the loss in current or power resulting from soiling conditions. The device may be computerized to monitor changes in the ratio and/or store and manipulate data relating to the efficiency of the PV device under test. The disclosed technology serves as a platform for PV device testing under soiling conditions. It can accommodate any mono-facial PV technology, thus allowing for a wide range of potential applications.

In an alternative embodiment, n separate stations may be used, where n is preferably an integer greater than or equal to three. In this embodiment, measurements of the short circuit current of a single photovoltaic device are made in response to exposure to illumination in first, second and third states. The first state is with the single photovoltaic device unobstructed and exposed directly to illumination at a first one of the n stations. The second state includes the photovoltaic device disposed at a $(j-1)^{th}$ station in a compartment exposed to illumination through a clean, transparent cover. The third state is with the single photovoltaic device disposed in a $j^{th}$ station in a compartment exposed to illumination through a transparent cover on which natural or simulated soil is permitted to accumulate without cleaning. The $(j-1)^{th}$ station and the $j^{th}$ station are adjacent to one another, where $2 \leq j \leq n$.

A soiling effectiveness index, SEI, may then be calculated as:

$$SEI = \frac{I_{sc_1} + I_{sc(j)} - I_{sc(j-1)}}{I_{sc_1} + I_{sc(j')} - I_{sc(j'-1)}}$$

where $I_{sc_1}$ is the short circuit current measured in the first initial state, $I_{sc(j-1)}$ and $I_{sc(j'-1)}$ are the short circuit currents measured at two clean states, and $I_{sc(j)}$ and $I_{sc(j')}$ are the short circuit currents measured at two soiled states. If SEI=1, then it can be determined that the transparent cover of the $j^{th}$ station is substantially as effective against soiling as the transparent cover of the $(j')^{th}$ station. If SEI>1, then it can be determined that the transparent cover of the $j^{th}$ station is more effective against soiling than the transparent cover of the $(j')^{th}$ station. If SEI<1, then it can be determined that the transparent cover of the $j^{th}$ station is less effective against soiling than the transparent cover of the $(j')^{th}$ station. The latter embodiment may be used to evaluate the suitability of photovoltaic covers that have been modified to reduce adhesion of soiling particles to the cover of a photovoltaic device, e.g., by coating the cover with a "self-cleaning" coating or by altering the composition of the photovoltaic glass used to make the cover. The method adds two additional test stations to the device for each modified cover to be tested, one test station with a modified cover cleaned periodically and the other with a modified cover left exposed to soiling, and compares the effectiveness of the modified cover(s) against a reference cover in the second state and the third state.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The device and method for measuring the effect of soiling on a photovoltaic (PV) device includes a device in which a PV device (solar cell, PV module, etc.) may be shifted between partially and fully enclosed compartments in quick succession for measurements of the same device (1) when directly exposed to illumination or solar radiation; (2) when placed under a transparent cover maintained clear or cleaned of soil; and (3) when placed under a transparent cover left exposed to soiling that is not periodically cleaned. The measurements may be of short circuit current ($I_{sc}$), maximum power ($P_{max}$), and/or other parameters conventionally used to evaluate performance of the PV device. Each measurement may be an instantaneous value or a measurement of changing values over a predetermined time interval; e.g., an I-V curve. A soiling ratio calculated as:

$$SR_{Pmax} = 1 - \frac{P_{max2} - P_{max3}}{P_{max1}}$$

or calculated as:

$$SR_{Isc} = 1 - \frac{I_{sc2} - I_{sc3}}{I_{sc1}}$$

may be used to compare or monitor effectiveness of the PV device between measurement cycles.

To capture the soiling effect using a single device, the PV device is required to be measured under three different states. State 1 will be the initial state where the $I_{sc}$, $P_{max}$, and/or other parameters of the PV device are measured. The device will then move to State 2, and a similar measurement to the initial state, State 1, will be taken under a clean transparent cover. For the final state, State 3, the same measurement will be repeated under a soiled (i.e., never cleaned) transparent cover. Because the extra layer of transparent cover in States 2 and 3 will introduce an additional power loss, measurements in all three states need to be mathematically compensated for this extra layer. To further ensure accuracy, all three states will be measured in a sufficiently short period of time. Any deviations in PV temperature and/or amount of sunlight received from the states will be normalized. This process allows for the computation of the Soiling Ratio (SR) as an indicator of PV performance loss resulting from soiling. Since the new disclosed technology utilizes a single PV device, the SR will be expressed as:

$$SR_{Pmax} = \frac{P_{max\,dirty}}{P_{max\,clean}} = \frac{P_{max3} + (P_{max1} - P_{max2})}{P_{max1}} = 1 - \frac{P_{max2} - P_{max3}}{P_{max1}}$$

$$SR_{Isc} = \frac{I_{sc3} + (I_{sc1} - I_{sc2})}{I_{sc1}} = 1 - \frac{I_{sc2} - I_{sc3}}{I_{sc1}},$$

where SR is the Soiling Ratio, $P_{max}$ is the power at maximum power point, $I_{SC}$ is the short circuit current, and the subscripts 1, 2 and 3 refer to the State in which the measurement was made.

The use of a single PV device minimizes uncertainties stemming from complex differences that inherently exist between two similar, but nonidentical, devices. This provides a low-cost technique offering practical in-field use because it does not require cumbersome periodic operation and maintenance cycles. Furthermore, for an accurate soiling representation of a PV system, the user is not confined to a limited set of PV technologies (i.e., some products supply only one type), but broadens the scope of work to accommodate any desired mono-facial technology. Ultimately, the technique is intended to provide a reliable, practical and affordable soiling monitoring system for widespread applications that extend from research to industry. In particular, this technique advances the optimization of PV cleaning cycles and cost, monitoring energy production losses due to soiling, studying the effectiveness of new anti-soiling surface coatings, and the collection of site-specific data.

According to the method, three consecutive $I_{SC}$, $P_{max}$, and/or other parameter measurements of the PV device are taken, first, under no transparent cover (State 1), then under a clean transparent cover (State 2), and finally under a soiled transparent cover (State 3). These measurements can be achieved in a sufficiently short period of time. Measuring one PV device can effectively eliminate the uncertainties stemming from two nonidentical devices. The disclosed technology can be a standalone system where no external power supply is needed to allow installation in remote areas.

Software may be provided to enable the user to monitor and control the sensor system. Features such as data analysis, data presentation, and data extraction can be included because of the use of a direct calculation of soiling loss. As part of the data acquisition system, software may be provided in any convenient form, such as a desktop, as web-based software, or using a handheld device. The software can also be integrated with the data acquisition system. The system may execute functions including, but not limited to, the following: receive data of physical variables; process data; provide a graphical user interface; offer analytic tools for researchers and industry; forecast and compute optimal cleaning time; export records and reports in text or other portable data formats; detect system faults; configure features of system hardware, such as motor and fan speeds; and integrate with standard SCADA systems for PV power plants. In addition to the above-mentioned features, the software may have built-in features that would allow a user, such as an administrator, to change the way data is organized, computed and filtered, which allows for device optimization.

Figure 1A:
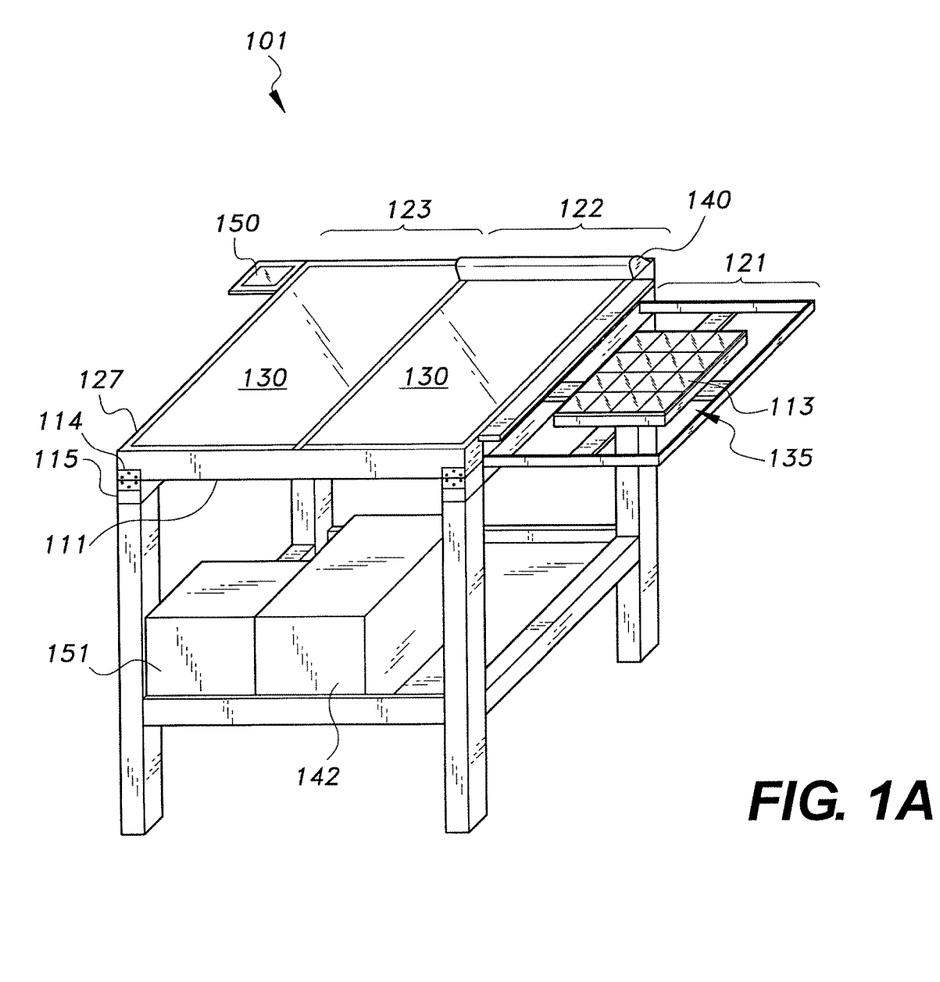
FIG. 1A is a perspective view of a device for measuring the effect of soiling on a photovoltaic device, shown in its east-west (E-W) lateral orientation and largely schematic.
Figure 1B:
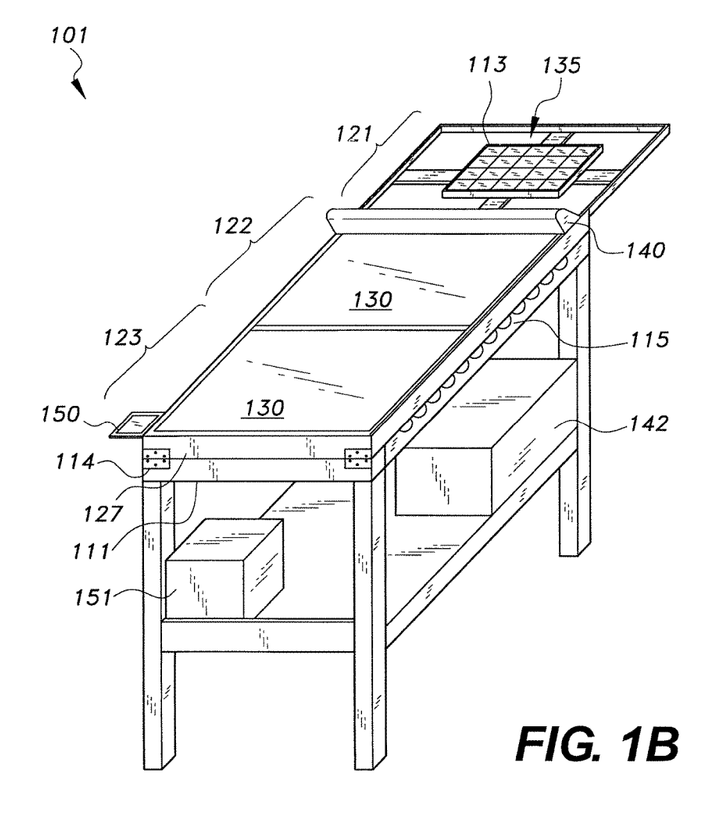
FIG. 1B is a perspective view of a device for measuring the effect of soiling on a photovoltaic device, shown in its north-south (N-S) axial orientation and largely schematic.

FIGS. 1A and 1B are schematic diagrams of a device 101 configured for measuring the effect of soiling on a photovoltaic device, shown in a lateral configuration and in an axial configuration, respectively. In the latter configuration, the PV device is measured along the north-south direction rather than the east-west direction between states, which yields higher measurement accuracy and allows for new parameters to be evaluated. Depicted is a frame housing 111 for testing a PV device, such as a PV module component 113, as a device under test (DUT). The device 101 has three test stations, 121, 122, 123, corresponding to the three measurement states, State 1—initial, State 2—clean and State 3—soiled. Test station 121 is only partially enclosed, being exposed directly to the outside environment for receiving illumination or solar radiation, whereas test stations 122 and 123 are provided as an enclosed compartment portion 127 of the device 101. A transparent cover 130, such as a tempered PV glass, forms a top of enclosed portion 127.

It is noted, however, that, at test station 123, the transparent cover 130 is soiled without any cleaning throughout the soiling monitoring cycle. The DUT 113 can be removed from its housing so that it can be characterized either by its original equipment manufacturer (OEM) or by an independent laboratory, when needed.

Nevertheless, the device 101 can be used to compare operational parameters in the three states, provided care is taken not to damage the DUT 113 during routine testing. In the device 101, the DUT is transported through stations 121, 122, and 123 to measure the electrical output at each station in a sufficiently short period of time such that environmental variations between the three measurements are kept to a minimum.

As can be seen in FIG. 1A, the DUT component 113 is shown outside of an enclosed portion of the device 101, but still supported by the device 101 at test station 121, corresponding to "State 1—initial". Both the DUT component 113 and the tray 135 holding it are coplanar with the other testing stations 122 and 123.

The DUT component 113 is then moved inside the device 101 to test station 122. Test station 122 is within the enclosed portion of the device 101, under a portion of the device 101 (a transparent cover 130) maintained in a clean state. Testing at test station 122 corresponds to "State 2—clean". In the enclosed portion of the device 101, light passes through a transparent cover 130, which, at test station 122, is maintained in a substantially clean condition.

The DUT component 113 is then moved inside the device 101 to test station 123. Test station 123 is within the enclosed portion 127 of the device 101, under a portion of the device 101 left in a soiled state. Testing at test station 123 corresponds to "State 3—soiled".

While a single enclosure is shown for test stations 122 and 123, it is understood that test stations 122 and 123 may be provided with separate enclosures, each with a separate transparent cover 130, but with station 123 in a soiled state. Likewise, a single test station can be used to provide the test operations of test stations 121, 122 and 123 with a single PV device, with the test station being changed by uncovering the DUT for State 1, covering the DUT with the clean transparent cover for State 2, and covering the DUT with the same or a different cover, but in a soiled state, for State 3.

The "State 3—soiled" condition can be adapted to outdoor local conditions. Examples of environmental debris or contamination can be dust from wind, vegetation debris, and soiling from birds or animal waste, all of which can vary according to the location of the test site.

The device 101 may have a support tray 135, which can be used to transport the DUT between the test stations, 121, 122, 123, either manually or automatically.

The device 101 is used to determine a performance difference between a clean state, described as "State 2—clean", and a soiled state, described as "State 3—soiled". The device 101 can then be used to determine the difference in electrical output when a PV device's surface becomes soiled.

Ventilation fans (not separately shown) may be used to reduce heat buildup until internal temperature and humidity sensor readings substantially agree with the ambient. When the DUT is at rest, and no measurements are being taken, the ventilation fans may operate to protect the internal components of the device 101 inside the enclosed compartment portion 127. Further, the enclosed compartment portion 127 can be opened for scheduled and unscheduled maintenance.

The cleaning of the transparent cover 130 may be done either manually or automatically using a built-in washer 140.

The device 101 may have a tilting mechanism component 114, which can adjust the tilt angle of test stations 121, 122, 123, the tray component 135, and the DUT component 113 concurrently between 0° (i.e., parallel to the ground) and 90° (i.e., perpendicular to the ground), either manually or automatically. The device 101 may also have a water tank 142 connected to the washer 140, an irradiance sensor 150, and a monitoring and control unit 151.

Figure 2:
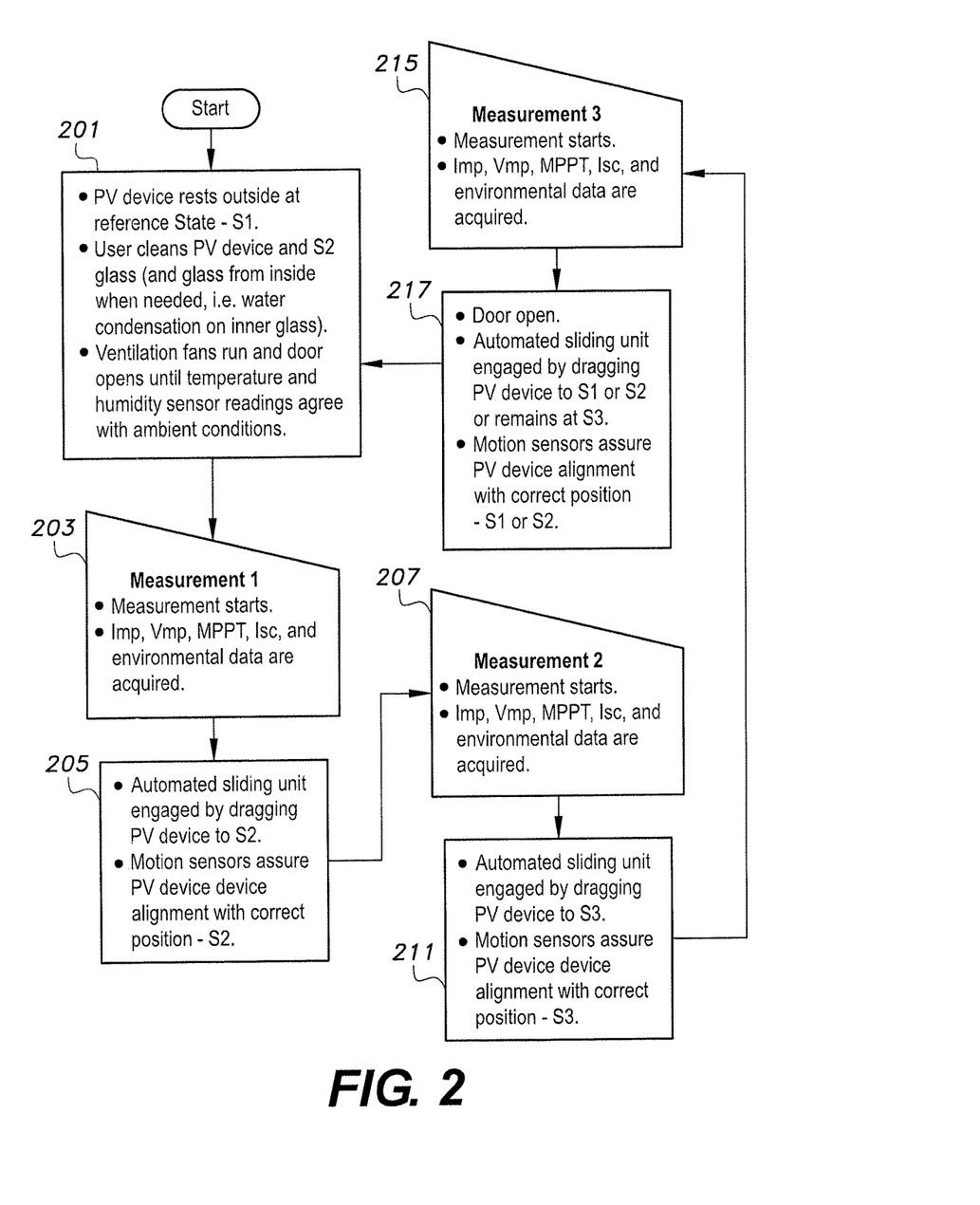
FIG. 2 is a flowchart showing mechanical steps in taking of measurements in three measurement states in a measurement cycle.

FIG. 2 is a flowchart showing one variation of the mechanics of taking measurements in States 1, 2 and 3. In each test sequence, testing is performed for short circuit current ($I_{sc}$), maximum power ($P_{max}$), and/or other criteria of the DUT component 113. Environmental data is also taken.

Referring to FIG. 2, the DUT is initially placed in a position outside the enclosure 127 of the device 101, and the test station 122 is cleaned, if needed (step 201). Measurement 1 is then taken (step 203). The DUT is then moved (step 205) into the enclosure 127 of the device 101 at test station 122 for testing in a clean state, as Measurement 2. The difference is that substantially all factors imposed by enclosing the DUT in enclosure 127 are present. The DUT is then tested (step 207). The DUT is then moved (step 211) for testing (step 215) in a soiled state, as Measurement 3. In the soiled state, the device's third test station 123 is either naturally soiled with dust and other environmental debris, or simulated dirt can be used at test station 123, and measurements are taken under those conditions (step 215), which is Measurement 3.

In an automated process, the DUT is placed in a position outside the enclosure of the device 101, and automated movement is achieved by motor controls to move the support tray 135. The support tray 135 transports the DUT for Measurements 1, 2, and 3 (with Measurement 1 performed before movement). This provides an automated acquisition of measurements for each test station where the DUT is evaluated.

On completion of the measurements, after obtaining Measurement 3 (step 215), the DUT is moved (step 217) to rest either at station 1, station 2, or remain at station 3 between measurement cycles.

One difference between Measurements 1 and 2 is that a baseline is established to account for losses due to the construction of the device 101 itself. In that way, the measurements taken under the regimes of Measurements 2 and 3 represent the changes resulting from the soiling represented by Measurement 3, with the effects of the device 101 cancelled out by the difference between Measurements 1 and 2.

Figure 3A:
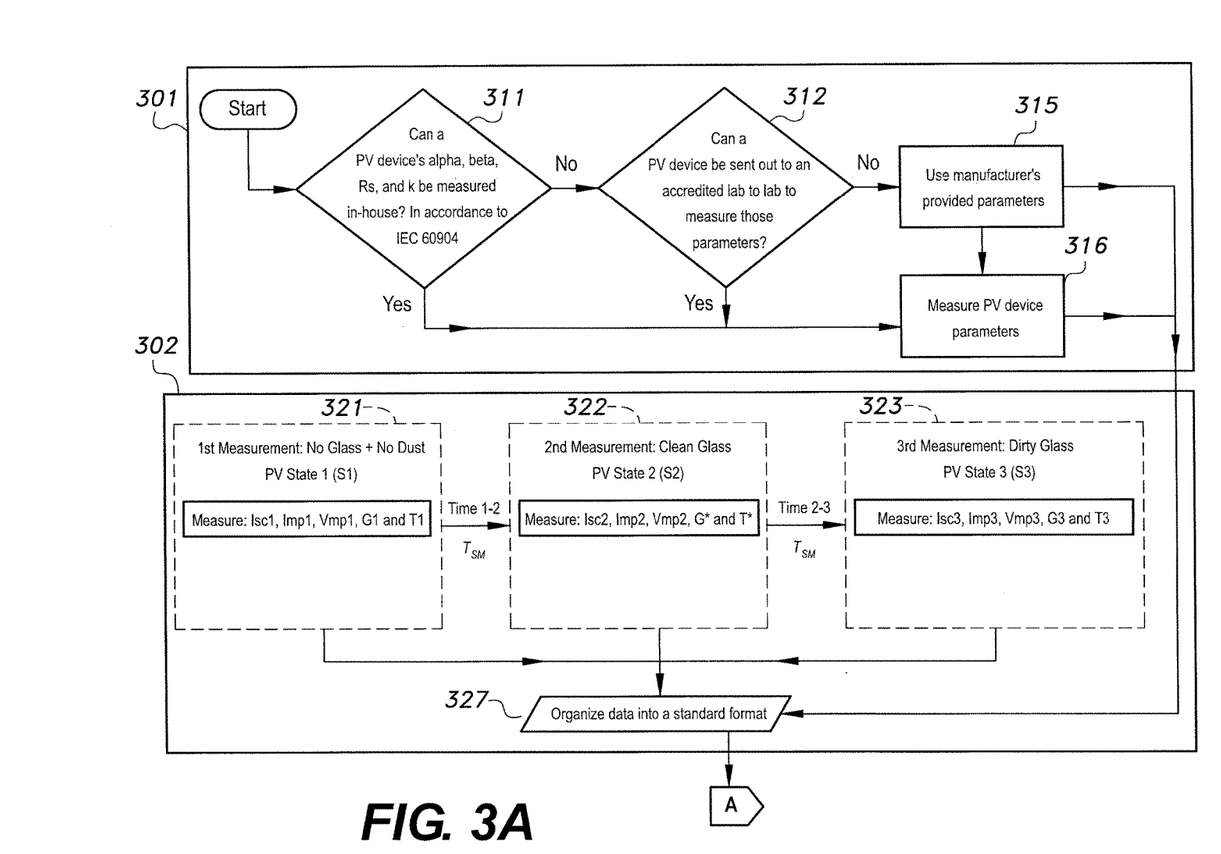
FIG. 3A, FIG. 3B, and FIG. 3C are a flowchart showing the steps in a method for measuring the effect of soiling on a photovoltaic device.
Figure 3B:
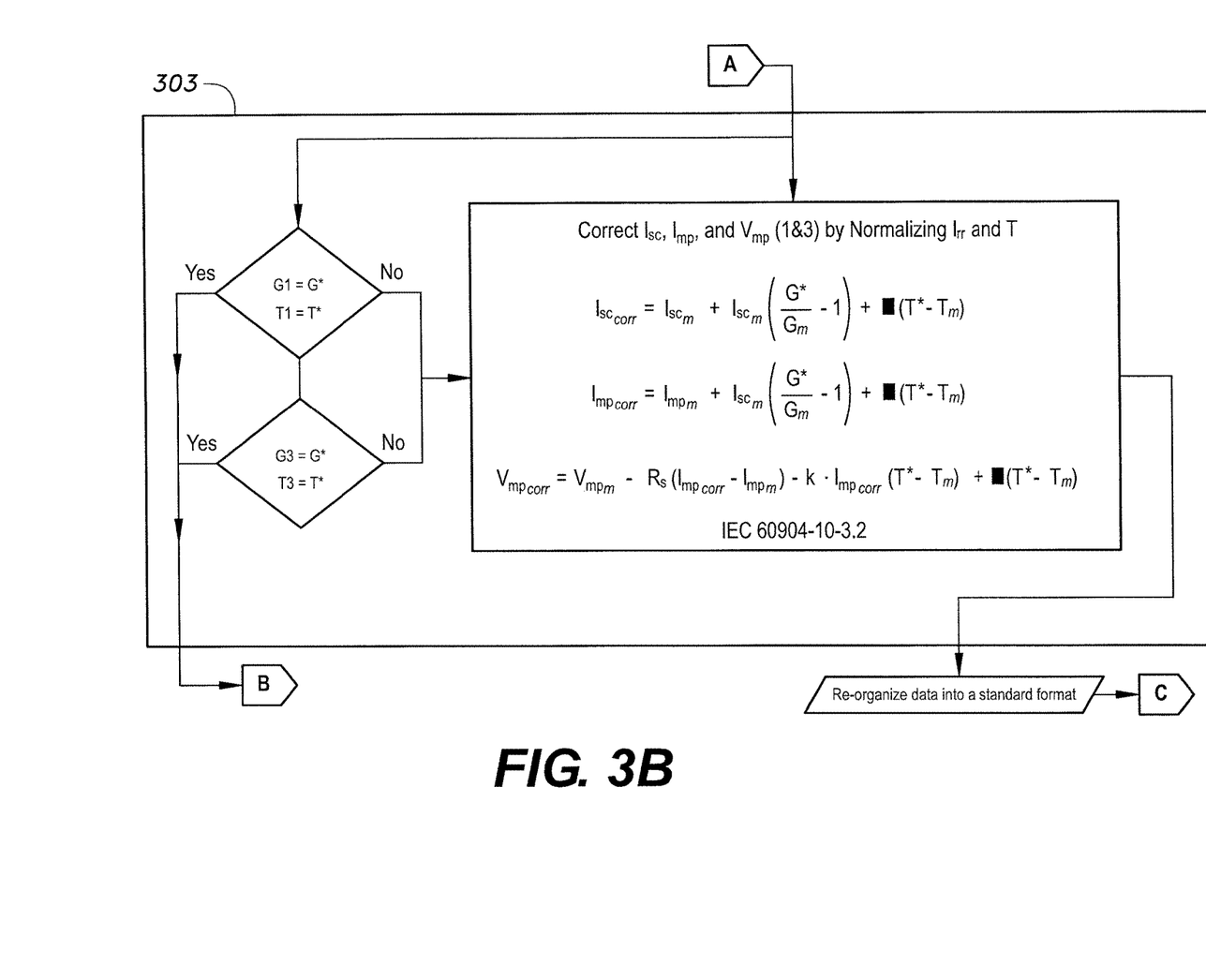
Figure 3C:
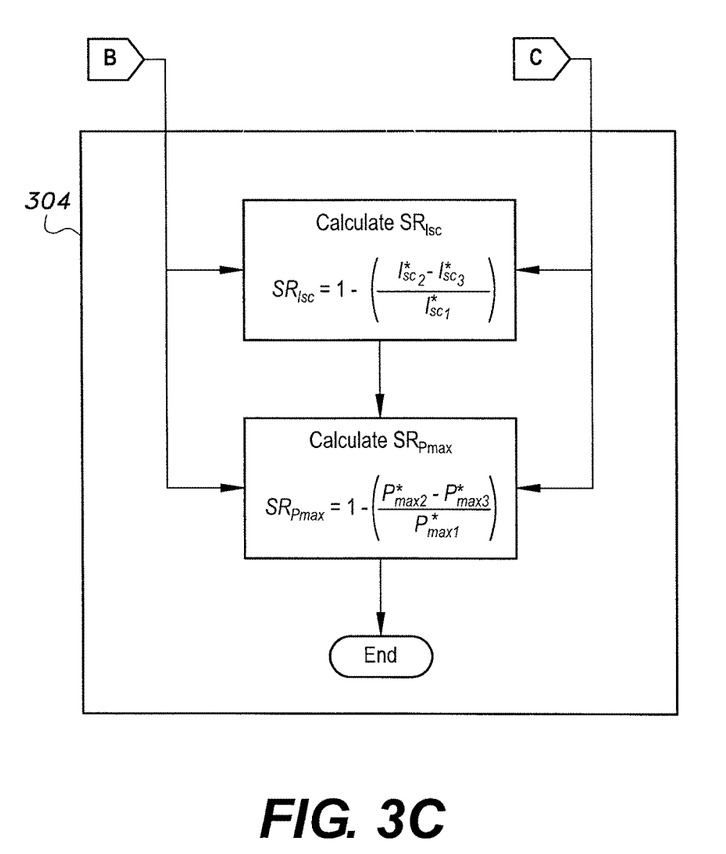

FIGS. 3A-3C are flowcharts showing the procedures and setup required for obtaining soiling measurements when using a single PV device. The process includes pre-installation 301, field measurements and data acquisition 302, normalizing weather conditions to a reference state 303 (i.e., State 2), and computation of the soiling ratio (SR) 304.

In the pre-installation step 301, a determination (step 311) is made of the ability to measure the PV device's alpha, beta, Rs and k values. Ideally, these values can be measured in the lab (in-house measurements) in accordance with IEC 60904. If it is not possible to obtain some of these measurements, a determination (step 312) is made as to whether measurements can be obtained from other accredited labs or supplied from another source. In either case, if these measurements cannot be made, then manufacturer-supplied parameters are used (step 315). If these values can be measured, then the device parameters are measured (step 316). Similarly, if some, but not all, parameters can be measured, then these parameters are used in combination with manufacturer-supplied parameters.

The parameters are provided for use in field measurements and data acquisition 302. Three measurements are used to obtain values for States 1, 2 and 3. In State 1, the measurement is taken with no transparent cover and the DUT is substantially clean (step 321). In State 2, a measurement is taken with clean transparent cover (step 322), and in State 3, a measurement is taken with soiled transparent cover (step 323). The measured data is organized into a standard format (step 327).

After obtaining the data for each of States 1, 2 and 3, normalized for weather conditions (step 303), a computation is made of a soiling ratio. In the normalization according to weather conditions (step 303), adjustments are made so that weather conditions as would affect the measurements are taken for State 2. These same adjustments are then applied to States 1 and 3. The normalized data is re-organized into a standard format (step 367) for use in the process for computing the soiling ratio (SR) (step 304).

Additional functions may be implemented within the scope of this disclosure, which may include combining an automatization capability to periodically clean the "clean transparent cover"" (required step) in addition to manual cleaning; providing an ability to both manually and automatically move the PV device from States 1, 2 and 3; development of a universal design to accommodate all PV sizes; combining the device with a weather station; moving the transparent cover of stations 2 and 3 over the fixed DUT at station 1 to make the three sequential measurements required; and combining the device with a solar simulator for indoor testing.

Figure 4:
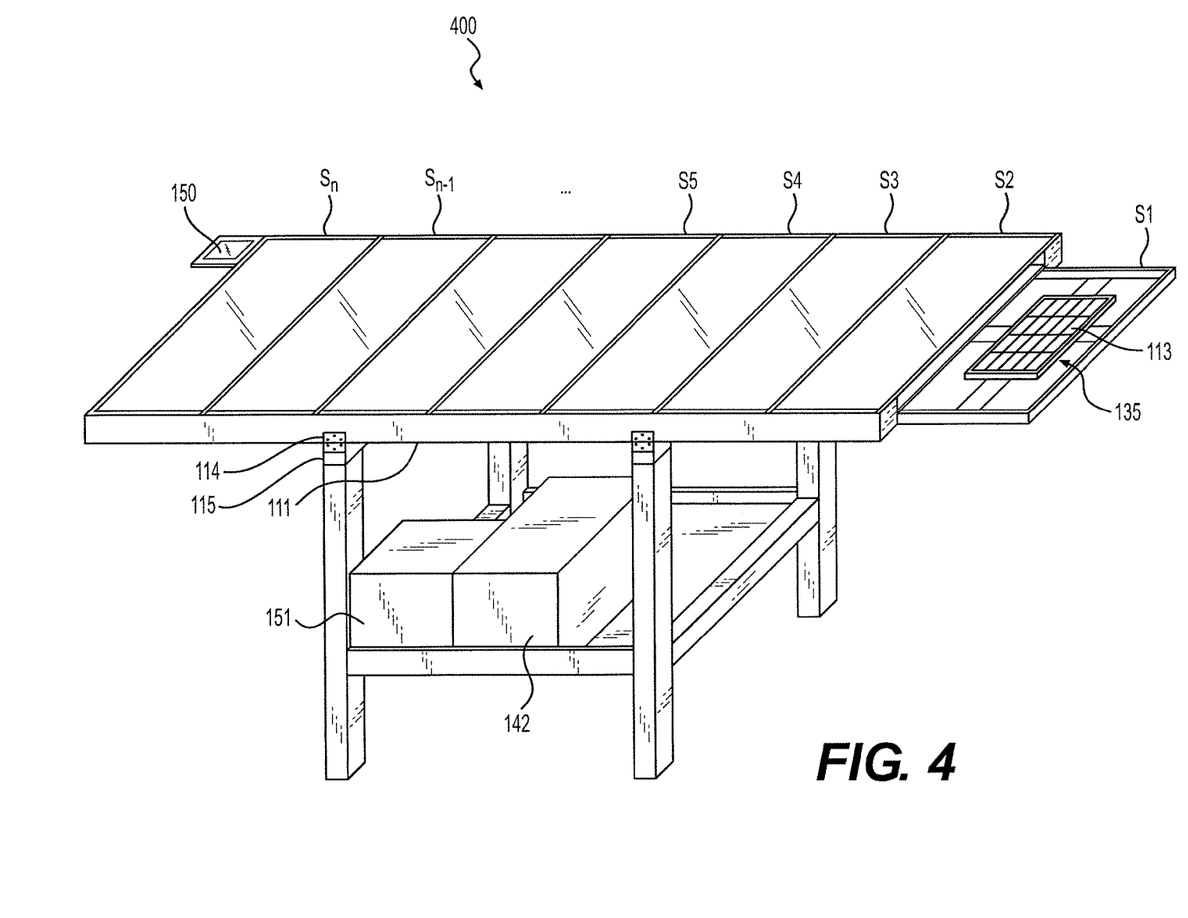
FIG. 4 is a perspective view of an alternative embodiment of a device for measuring the effect of soiling on a photovoltaic device and evaluating the performance of multiple anti-soiling solutions, largely schematic.

In the alternative embodiment of FIG. 4, the device for evaluating anti-soiling solutions and measuring the effect of soiling on a photovoltaic device 400 is similar to the device for measuring the effect of soiling on a photovoltaic device 101 of FIG. 1A. However, the device 400 includes n stations $S_1, S_2, \ldots S_{n-1}, S_n$, where n is preferably greater than or equal to three. Considering the case where the station j has a transparent cover that is soiled, and its adjacent station (the (j−1) station) has a clean, unsoiled transparent cover, then a generalized soiling ratio for the pair, denoted by:

$$SR_{\frac{j-1}{2}},$$

is given by:

$$SR_{\frac{j-1}{2}} = 1 - \frac{I_{sc_{(j-1)}}}{I_{sc_1}} + \frac{I_{sc_{(j)}}}{I_{sc_1}} = 1 - \left[\frac{I_{sc_{(j-1)}} - I_{sc_{(j)}}}{I_{sc_1}}\right],$$

where $I_{sc_1}$, $I_{sc_{(j-1)}}$ and $I_{sc_{(j)}}$ are measurements of short circuit current made in the first state, the (j−1) state, and the j state, respectively, and the values of j are the odd values of n greater than one, i.e., j=3, 5, 7, 9, . . . .

Soiling loss at different stations, that contain different anti-soiling solutions, can be compared to each other by the value of the soiling effectiveness index (SEI), which indicates the performance effectiveness of different transparent covers under a soiled condition:

$$SEI_{x,y} = \frac{SR_x}{SR_y},$$

where:

$$x: 1 \to \frac{j-1}{2}$$

and $$y: 1 \to \frac{j'-1}{2},$$

and where j' is an odd value of n that does not equal j.

The calculated $SEI_{x,y}$ values may be compared as follows: (a) if $SEI_{x,y}=1$, then the transparent cover of station j used to calculate $SR_x$ is either comparable to, or as effective against soiling, as the transparent cover of station j' used to calculate $SR_y$; (b) if $SEI_{x,y}>1$, then the transparent cover of station j used to calculate $SR_x$ is more effective against soiling than the transparent cover of station j' used to calculate $SR_y$, and thus the cover at station j is more favorable; and (c) if $SEI_{x,y}<1$, then the transparent cover of station j used to calculate $SR_x$ is less effective against soiling than the transparent cover of station j' used to calculate $SR_y$, thus the cover at station j' is more favorable.

The mathematical expression of $SEI_{x,y}$ can be expanded as:

$$SEI_{x,y} = \frac{SR_x}{SR_y} = \frac{I_{sc_1} + I_{sc_{(j)}} - I_{sc_{(j-1)}}}{I_{sc_1} + I_{sc_{(j')}} - I_{sc_{(j'-1)}}}.$$

The opto-electrical loss factor (OLF) indicates the amount of loss in the electrical outputs due to the existence of the clean cover at the (j−1) station, and may be calculated as:

$$OLF_{(j-1)} = 1 - \frac{I_{sc_{(j-1)}}}{I_{sc_1}}.$$

The value of this parameter favors the solution that introduces less optical loss. However, in the case of anti-soiling solutions, the OLF values should be analyzed in the shadow of the SEI values, since some solutions could introduce less optical loss, but high soiling loss values. The mathematical expression of OLF can be expanded as:

$$OLF_{(j-1)} = \frac{I_{sc_1} - I_{sc_{(j-1)}}}{I_{sc_1}}.$$

The clean cover performance ratio (CCPR) indicates the effect of the modified cover on the PV device performance relative to another cover when both are in clean condition:

$$CCPR_{(j-1),(j'-1)} = \frac{OLF_{(j-1)}}{OLF_{(j'-1)}}.$$

The calculated $CCPR_{(j-1),(j'-1)}$ values may be compared as follows: (a) if $CCPR_{(j-1),(j'-1)}=1$, then the transparent cover of the clean (j−1) station is either comparable to, or as effective as, the transparent cover of clean (j'−1) station, i.e., both covers have the same optical effect on PV device performance; (b) if $CCPR_{(j-1),(j'-1)}>1$, then the transparent cover of clean (j−1) station affects the PV device performance more than the transparent cover of clean (j'−1) station, and thus the cover at clean (j'−1) station is more favorable, since it results in lower optical loss values; and (c) if $CCPR_{(j-1),(j'-1)}<1$, then the transparent cover of clean (j'−1) station affects the PV device performance more than the transparent cover of clean (j−1) station, and thus the cover at clean (j−1) station is more favorable, since it results in lower optical loss values.

The mathematical expression of $CCPR_{(j-1),(j'-1)}$ can be expanded as:

$$CCPR_{(j-1),(j'-1)} = \frac{I_{sc_1} - I_{sc_{(j-1)}}}{I_{sc_1} - I_{sc_{(j'-1)}}}.$$

When evaluating several solutions, such as self-cleaning coatings that can be applied on the same type of clean cover that is installed in the second station, then the generalized soiling ratio will be:

$$SR_i = 1 - \frac{I_{sc_2}}{I_{sc_1}} + \frac{I_{sc_i}}{I_{sc_1}} = 1 - \left[ \frac{I_{sc_2} - I_{sc_i}}{I_{sc_1}} \right],$$

where i denotes the soiled station values i=3→n. In this particular case, station $S_2$ is considered to be the only clean station with a clean transparent cover. Stations i contain coated covers in soiled conditions. Device 400, in this case, is capable of evaluating several coatings under the same conditions with a single PV device. The soiling loss, given as SL=1−SR, can then be easily calculated from the above.

Alternatively, SR can be calculated using only two stations, where the clean cover can be removed from the overall structure and measurements can be taken for the PV device with no cover. This can be performed along with a second measurement taken when the clean cover is still attached. Then, a third measurement of the PV device can be taken at the station with the soiled cover. As a further alternative, measurements can be taken at only a single station, with three measurements respectively being taken for the case with no cover, a clean cover, and the clean cover replaced with a soiled cover.

It is to be understood that the device and method for measuring the effect of soiling on a PV device are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method for measuring effectiveness of a modified photovoltaic device cover for reducing adverse effects of soiling on the photovoltaic device, comprising the steps of:
 exposing a single test photovoltaic device to irradiation by a light source at a first test station of a measurement device and measuring short circuit current ($I_{SC_1}$) of the single test photovoltaic device during the irradiation, the first test station exposing the single test photovoltaic device directly to a source of the irradiation without an intervening cover;

moving the single test photovoltaic device to a second test station of the measurement device, exposing the single test photovoltaic device to irradiation by a light source at the second test station of the measurement device, and measuring short circuit current ($I_{SC_{(j-1)}}$) of the single test photovoltaic device during the irradiation, the second test station exposing the single test photovoltaic device to a source of the irradiation with an intervening clean, transparent, reference photovoltaic cover, the clean reference photovoltaic cover being maintained in clean condition by periodic cleaning;

moving the single test photovoltaic device to a third test station of the measurement device, exposing the single test photovoltaic device to irradiation by a light source at the third test station of the measurement device, and measuring short circuit current ($I_{SC_{(j)}}$) of the single test photovoltaic device during the irradiation, the third test station exposing the single test photovoltaic device to a source of the irradiation with an transparent reference photovoltaic cover left exposed to soiling;

moving the single test photovoltaic device to a fourth test station of the measurement device, exposing the single test photovoltaic device to irradiation by a light source at the fourth test station of the measurement device, and measuring short circuit current ($I_{SC_{(j'-1)}}$) of the single test photovoltaic device during the irradiation, the fourth test station exposing the single test photovoltaic device to a source of the irradiation with an intervening clean, transparent, modified photovoltaic cover, the clean modified photovoltaic cover being modified to reduce the effects of soiling;

moving the single test photovoltaic device to a fifth test station of the measurement device, exposing the single test photovoltaic device to irradiation by a light source at the fifth test station of the measurement device, and measuring short circuit current ($I_{SC_{(j')}}$) of the single test photovoltaic device during the irradiation, the fifth test station exposing the single test photovoltaic device to a source of the irradiation with an intervening transparent, modified photovoltaic cover left exposed to soiling, the modified photovoltaic cover being modified to reduce the effects of soiling;

calculating ratios of the measured short circuit currents to compare the effectiveness of the single test photovoltaic device when exposed to irradiation with the intervening reference photovoltaic device against the effectiveness of the single test photovoltaic device when exposed to irradiation with the intervening modified photovoltaic cover; and selecting the intervening photovoltaic cover for the photovoltaic device shown by the calculated ratios to leave the single test photovoltaic device most effective.

2. The method for measuring effectiveness of a modified photovoltaic device cover according to claim 1, wherein said modified photovoltaic cover comprises a transparent photovoltaic cover having a self-cleaning coating for reducing adhesion of soiling particles on the photovoltaic cover.

3. The method for measuring effectiveness of a modified photovoltaic device cover according to claim 1, wherein said modified photovoltaic cover comprises a transparent photovoltaic cover having a different composition from the reference photovoltaic cover for reducing adhesion of soiling particles on the photovoltaic cover.

4. The method for measuring effectiveness of a modified photovoltaic device cover according to claim 1, wherein said step of calculating ratios includes calculating a soiling ratio of the second and third test stations according to the formula:

$$SR_{\frac{j-1}{2}} = 1 - \frac{I_{sc_{(j-1)}}}{I_{sc_1}} + \frac{I_{sc_{(j)}}}{I_{sc_1}} = 1 - \left[\frac{I_{sc_{(j-1)}} - I_{sc_{(j)}}}{I_{sc_1}}\right];$$

and computing a soiling ratio for the fourth and fifth test stations according to the formula:

$$SR_{\frac{j'-1}{2}} = 1 - \frac{I_{sc_{(j'-1)}}}{I_{sc_1}} + \frac{I_{sc_{(j')}}}{I_{sc_1}} = 1 - \left[\frac{I_{sc_{(j'-1)}} - I_{sc_{(j')}}}{I_{sc_1}}\right].$$

5. The method for measuring effectiveness of a modified photovoltaic device cover according to claim 4, wherein said step of calculating ratios includes calculating a soiling effectiveness index (SEI) according to the formula:

$$SEI_{x,y} = \frac{SR_x}{SR_y},$$

where:

$$x: 1 \to \frac{j-1}{2}$$

and $$y: 1 \to \frac{j'-1}{2}.$$

6. The method for measuring effectiveness of a modified photovoltaic device cover according to claim 4, wherein said step of calculating ratios includes calculating a soiling effectiveness index (SEI) according to the formula:

$$SEI_{x,y} = \frac{SR_x}{SR_y} = \frac{I_{sc_1} + I_{sc_{(j)}} - I_{sc_{(j-1)}}}{I_{sc_1} + I_{sc_{(j')}} - I_{sc_{(j'-1)}}}.$$

7. The method for measuring effectiveness of a modified photovoltaic device cover according to claim 1, wherein said step of calculating ratios includes calculating an optoelectrical loss factor (OLF) according to the formula:

$$OLF_{(j-1)} = 1 - \frac{I_{sc_{(j-1)}}}{I_{sc_1}}.$$

8. The method for measuring effectiveness of a modified photovoltaic device cover according to claim 1, wherein said step of calculating ratios includes calculating an optoelectrical loss factor (OLF) according to the formula:

$$OLF_{(j-1)} = \frac{I_{sc_1} - I_{sc_{(j-1)}}}{I_{sc_1}}.$$

9. The method for measuring effectiveness of a modified photovoltaic device cover according to claim 8, wherein said step of calculating ratios includes calculating a clean cover performance ratio (CCPR) according to the formula:

$$CCPR_{(j-1),(j'-1)} = \frac{OLF_{(j-1)}}{OLF_{(j'-1)}}.$$

10. The method for measuring effectiveness of a modified photovoltaic device cover according to claim 1, wherein said step of calculating ratios includes calculating a clean cover performance ratio (CCPR) according to the formula:

$$CCPR_{(j-1),(j'-1)} = \frac{I_{sc_1} - I_{sc_{(j-1)}}}{I_{sc_1} - I_{sc_{(j'-1)}}}.$$

11. The method for measuring effectiveness of a modified photovoltaic device cover according to claim 1, wherein said step of calculating ratios includes calculating a soiling ratio according to the formula:

$$SR_i = 1 - \frac{I_{sc_2}}{I_{sc_1}} + \frac{I_{sc_i}}{I_{sc_1}} = 1 - \left[\frac{I_{sc_2} - I_{sc_i}}{I_{sc_1}}\right],$$

wherein i denotes an index of test stations having a soiled transparent photovoltaic cover selected from i=3→n, and wherein $I_{sc_2}$ represents the short circuit current measured with a sole clean transparent cover.

12. The method for measuring effectiveness of a modified photovoltaic device cover according to claim 1, further comprising the step of repeating the moving, exposing, and measuring steps for additional pairs of clean and soiled modified photovoltaic covers corresponding to additional modified photovoltaic covers to be tested.

13. A method for measuring an effect of soiling on a photovoltaic device, comprising the steps of:
making measurements of a short circuit current of a single photovoltaic device in response to exposure to illumination in first, second and third states, the first state being with the single photovoltaic device unobstructed and exposed directly to illumination at a first of n stations, where n is an integer greater than or equal to three, the second state being with the photovoltaic device disposed at a (j-1) station in a compartment exposed to illumination through a clean transparent cover, and the third state being with the photovoltaic device disposed in a station j in a compartment exposed to illumination through a transparent cover on which natural or simulated soil is permitted to accumulate without cleaning, the (j-1) station and the j station being adjacent to one another, wherein 2<j≤n;
calculating a soiling effectiveness index, SEI, as:

$$SEI = \frac{I_{sc_1} + I_{sc_{(j)}} - I_{sc_{(j-1)}}}{I_{sc_1} + I_{sc_{(j')}} - I_{sc_{(j'-1)}}}$$

wherein $I_{sc_1}$ is the short circuit current measured in the first state, $I_{sc_{(j-1)}}$ and $I_{sc_{(j'-1)}}$ are short circuit currents measured in the second and clean states, and $I_{sc_{(j)}}$ and $I_{sc_{(j')}}$ are short circuit currents measured in the third and soiled states; and
if SEI=1, then determining that the transparent cover of the j station is substantially as effective against soiling as the transparent cover of the $j^{th}$ station, if SEI>1, then determining that the transparent cover of the j station is more effective against soiling than the transparent cover of the j' station, and if SEI<1, then determining that the transparent cover of the j station is less effective against soiling than the transparent cover of the j' station.

14. The method for measuring an effect of soiling on a photovoltaic device as recited in claim 13, further comprising the steps of:
making a measurement of a short circuit current of the single photovoltaic device in response to exposure to illumination in a fourth state, wherein the fourth state includes the single photovoltaic device being disposed at a (j'-1) station in a compartment exposed to illumination through a secondary clean transparent cover;
calculating an opto-electrical loss factor for the second state, $OLF_{(j-1)}$, as:

$$OLF_{(j-1)} = \frac{I_{sc_1} - I_{sc_{(j-1)}}}{I_{sc_1}};$$

calculating an opto-electrical loss factor for the fourth state, $OLF_{(j'-1)}$, as:

$$OLF_{(j'-1)} = \frac{I_{sc_1} - I_{sc_{(j'-1)}}}{I_{sc_1}},$$

where $I_{sc_{(j'-1)}}$ is the short circuit current measured in the fourth state.

15. The method for measuring an effect of soiling on a photovoltaic device as recited in claim 14, further comprising the steps of:
calculating a clean cover performance ratio, $CCPR_{(j-1),(j'-1)}$, as:

$$CCPR_{(j-1),(j'-1)} = \frac{OLF_{(j-1)}}{OLF_{(j'-1)}};$$

and
if $CCPR_{(j-1),(j'-1)}=1$, then determining that the transparent cover of the (j-1) station is substantially equally as effective as the transparent cover of the (j'-1) station, if $CCPR_{(j-1),(j'-1)}>1$, then determining that the transparent cover of the (j-1) station has lower optical loss values than those of the (j-1) station; and if $CCPR_{(j-1),(j'-1)}<1$, then determining that the transparent cover of the (j-1) station has lower optical loss values than those of the (j'-1) station.

* * * * *